(12) United States Patent
Majercak

(10) Patent No.: US 7,306,617 B2
(45) Date of Patent: *Dec. 11, 2007

(54) SPIRAL CENTERING CATHETER

(75) Inventor: David C. Majercak, Stewartsville, NJ (US)

(73) Assignee: Cordis Corporation, Miami Lakes, FL (US)

( * ) Notice: Subject to any disclaimer, the term of this patent is extended or adjusted under 35 U.S.C. 154(b) by 171 days.

This patent is subject to a terminal disclaimer.

(21) Appl. No.: 10/973,583

(22) Filed: Oct. 26, 2004

(65) Prior Publication Data

US 2005/0171592 A1     Aug. 4, 2005

Related U.S. Application Data

(63) Continuation-in-part of application No. 10/178,434, filed on Jun. 24, 2002, now Pat. No. 6,932,829.

(51) Int. Cl.
*A61M 29/00* (2006.01)

(52) U.S. Cl. .......................... 606/198; 604/96.01; 600/4

(58) Field of Classification Search ................ 604/508, 604/509, 510, 96.01, 103.04, 103.09, 104, 604/105, 523, 912; 606/191, 192, 194, 198
See application file for complete search history.

(56) References Cited

U.S. PATENT DOCUMENTS

| | | | | |
|---|---|---|---|---|
| 4,762,130 A | * | 8/1988 | Fogarty et al. ............. 606/159 |
| 5,284,486 A | * | 2/1994 | Kotula et al. ............... 606/159 |
| 5,295,959 A | * | 3/1994 | Gurbel et al. .......... 604/103.13 |
| 5,308,356 A | * | 5/1994 | Blackshear et al. ......... 606/194 |
| 5,383,856 A | * | 1/1995 | Bersin .................... 604/101.01 |
| 5,415,634 A | * | 5/1995 | Glynn et al. ........... 604/103.08 |
| 5,421,832 A | | 6/1995 | Lefebvre |
| 5,540,659 A | * | 7/1996 | Teirstein ...................... 604/104 |
| 5,551,443 A | * | 9/1996 | Sepetka et al. ............. 600/585 |
| 5,643,171 A | * | 7/1997 | Bradshaw et al. ............. 600/1 |
| 5,755,708 A | * | 5/1998 | Segal ........................... 604/107 |
| 5,797,948 A | * | 8/1998 | Dunham ...................... 606/194 |
| 5,840,067 A | | 11/1998 | Berguer et al. |
| 5,851,171 A | * | 12/1998 | Gasson .......................... 600/3 |
| 5,882,290 A | * | 3/1999 | Kume ............................ 600/3 |
| 5,891,091 A | * | 4/1999 | Teirstein ...................... 604/104 |
| 5,910,101 A | | 6/1999 | Andrews et al. |
| 5,938,582 A | * | 8/1999 | Ciamacco et al. ............. 600/3 |

(Continued)

FOREIGN PATENT DOCUMENTS

WO    WO 01/37746 A1    5/2001

(Continued)

*Primary Examiner*—Catherine S. Williams
(74) *Attorney, Agent, or Firm*—Michael W. Montgomery

(57) ABSTRACT

A catheter with proximal and distal ends having a spiral centering device attached near the catheter distal end. The spiral centering device has at least one spiral strut having a proximal end and a distal end. The spiral centering device resiliently tends to center the distal end portion of the catheter, steering the catheter away from the vessel wall during insertion through the vasculature and toward the treatment site. The spiral centering catheter may facilitate access to tortuous anatomy by preventing the distal catheter tip from catching on irregularities in the lumenal surface. If a stent is provided on the catheter, the spiral centering catheter may also facilitate uniform stent expansion by stabilizing the catheter during stent deployment.

13 Claims, 3 Drawing Sheets

U.S. PATENT DOCUMENTS

| | | | |
|---|---|---|---|
| 5,947,924 A * | 9/1999 | Liprie | 604/103.07 |
| 5,951,458 A * | 9/1999 | Hastings et al. | 600/3 |
| 5,984,957 A * | 11/1999 | Laptewicz et al. | 623/1.15 |
| 6,024,756 A | 2/2000 | Huebsch et al. | |
| 6,190,356 B1 * | 2/2001 | Bersin | 604/101.01 |
| 6,210,312 B1 | 4/2001 | Nagy | |
| 6,213,976 B1 | 4/2001 | Trerotola | |
| 6,224,535 B1 | 5/2001 | Chiu et al. | |
| 6,267,775 B1 | 7/2001 | Clerc et al. | |
| 6,280,414 B1 | 8/2001 | Shah et al. | |
| 6,338,709 B1 | 1/2002 | Geoffrion et al. | |
| 6,379,380 B1 | 4/2002 | Satz | |
| 6,450,988 B1 * | 9/2002 | Bradshaw | 604/96.01 |
| 6,514,191 B1 | 2/2003 | Popowski et al. | |
| 6,529,756 B1 | 3/2003 | Phan et al. | |
| 6,533,753 B1 | 3/2003 | Haarstad et al. | |
| 6,544,278 B1 | 4/2003 | Vrba et al. | |
| 6,547,812 B1 | 4/2003 | Hu | |
| 6,585,715 B1 * | 7/2003 | Teirstein | 604/508 |
| 6,932,829 B2 * | 8/2005 | Majercak | 606/198 |
| 2002/0010489 A1 | 1/2002 | Grayzel et al. | |
| 2005/0177130 A1 * | 8/2005 | Konstantino et al. | 604/509 |

FOREIGN PATENT DOCUMENTS

| | | |
|---|---|---|
| WO | WO 01/76525 A2 | 10/2001 |
| WO | WO 01/89412 A2 | 11/2001 |

* cited by examiner

SPIRAL CENTERING CATHETER

CROSS-REFERENCE To RELATED APPLICATION

The present application is a continuation-in-part of Ser. No. 10/178,434, entitled "Centering Catheter" filed Jun. 24, 2002 now U.S. Pat. No. 6,932,829.

BACKGROUND AND SUMMARY OF THE INVENTION

1. Technical Background

The present invention relates to a catheter, and more particularly to a catheter with a spiral centering tip.

2. Discussion

Percutaneous transluminal coronary angioplasty (PTCA), percutaneous transluminal angioplasty (PTA), and stenting are therapeutic medical procedures used to increase blood flow through blood vessels, and can often be used as alternatives to coronary bypass surgery. In angioplasty procedures, a balloon is inflated within a narrowed or stenosed vessel, at a desired location for treatment, such as an atheroma or plaque deposit, in order to obtain an enlarged opening or lumen. In stenting, an endoluminal prosthesis of any appropriate type is implanted in the vessel to maintain patency and hold open the vessel following the procedure. In order to initiate these procedures, a physician first introduces a guidewire into a passage or lumen of a vessel to serve as a conduit for other interventional devices, such as angioplasty balloons and stent delivery systems. This guidewire is advanced to a position past the location of a stenosis. Additional interventional devices, such as angioplasty balloon catheters and stent delivery systems, are then advanced over the guidewire and positioned at the site of the stenosis, to initiate therapeutic treatment of the lesion.

A common treatment method for using such an angioplasty balloon catheter or stent delivery system is to advance the catheter into the body of a patient over the guidewire, by directing the catheter distal end percutaneously through an incision and along a body passage until the device is located within the desired site. One commonly encountered challenge with the procedure involves irregularities of the lumenal surface and narrowing of the passageway, because the distal end of the balloon catheter or the stent delivery system may "catch" on the wall surface. This may cause a challenge in reaching the desired position in the vessel, and therefore may inhibit successful treatment of the lesion. Another difficulty that may be encountered with this procedure is that once the lesion is reached, stent deployment may not be perfectly uniform if the stent delivery system is not centered within the vessel, resulting in non-uniform deployment. The end result may be reduced strength and incomplete stent scaffolding of the vessel, and a less than optimal clinical result.

The general concept of a centering catheter for treating a body vessel with a radioactive source is known in the art. See, for example, U.S. Pat. No. 6,224,535 entitled "Radiation Centering Catheters" issued May 1, 2001, and U.S. Pat. No. 6,267,775 entitled "Self-Expanding Medical Device For Centering Radioactive Treatment Sources In Body Vessels" issued Jul. 31, 2001.

However, it is desirable to provide a device for centering a balloon catheter or stent delivery system during its journey through the vasculature or other anatomy and to the treatment site, to facilitate access to tortuous anatomy, and then to promote uniform deployed stent expansion at the treatment site.

According to the principles of the present invention, a centering catheter has a distal portion which tends to remain centered during its entire journey through anatomy and toward the desired treatment site, as well as at the treatment site.

This disclosure of the present invention will include various possible features and embodiments. However, the present invention scope is set for the in each of the claims, and is not limited to the particular arrangements described in this disclosure.

An object of the present invention is to facilitate access to tortuous anatomy, so that a lesion location may be more easily reached and the vessel may be treated. Another object of the present invention is to facilitate uniform deployed stent expansion by providing a centering catheter for stabilizing a stent delivery system catheter and centering it in the vessel during stent deployment.

Centering catheters may have an elongated catheter body with a proximal end and a distal end, and at least one spiral centering device attached near the distal end of the catheter. The spiral centering device may have a proximal end and a distal end and at least one spiral strut extending therebetween. The spiral centering device has a smaller diameter for insertion into a lumen, and a larger diameter for expanding to substantially equal the diameter of the lumen and to center a distal portion of the catheter within the lumen. The spiral centering device also has a plurality of intermediate diameters, between the smaller diameter and the larger diameter. These intermediate diameters may be utilized as the spiral centering device adjusts to diameter variations in the lumen of the vessel during the catheter journey through the vasculature and toward the treatment site.

Once the site is accessed, the spiral entering centering device may also facilitate uniform stent delivery for either balloon expandable or self-expanding stents, by centering the distal end of the catheter during the deployment of the stent. Uniform stent expansion may contribute to a successful clinical outcome. The spiral centering catheter and other devices may then be withdrawn from the lumen of the vessel.

In accordance with one aspect, a catheter may have at least one spiral centering device attached near a distal end of the catheter. Each spiral centering device has a proximal end and a distal end, and at least one strut extending therebetween. Each spiral centering device may have a variable diameter that tends to center the distal end of the catheter, steering the distal portion of the catheter away from the vessel wall during its insertion through the body passage to the treatment site.

In accordance with another aspect, a stent delivery system may have at least one spiral centering device attached near the distal end of the stent delivery system. Each spiral centering device may have a proximal end and a distal end, and at least one spiral strut extending therebetween. Each spiral centering device preferably has a variable diameter that tends to center the distal end of the catheter during stent deployment.

An advantage of the present invention is that the sometimes-tortuous anatomy of the vasculature may be more easily traversed while avoiding adverse lumen contact, and access to the lesion location may be facilitated by the availability of a spiral centering device that tends to center the distal portion of the catheter throughout its introduction into the vessel or other anatomy. Another advantage of the present invention is that the spiral centering device may stabilize the distal end of the catheter during stent expansion, and may therefore allow a physician to achieve a more uniform stent expansion with resultant clinical benefits to the patient.

These and various other objects, advantages and features of the resent invention will become apparent from the following description and claims, in conjunction with the appended drawings.

BRIEF DESCRIPTION OF DRAWINGS

The foregoing and other aspects of the present invention will best be appreciated with reference to the detailed description of the invention in conjunction with the accompanying drawings, wherein.

DETAILED DESCRIPTION OF THE PREFERRED EMBODIMENTS

The following description of the preferred embodiments of the present invention is merely illustrative in nature, and as such it does not limit in any way the present invention, its application, or uses. Numerous modifications may be made by those skilled in the art without departing from the true spirit and scope of the invention.

Centering catheters according to the principles of the present invention are designed to facilitate access to a treatment site in a lumen of a body passage through anatomy which may be tortuous, and/or to facilitate uniform stent deployment at a treatment site. A spiral centering catheter of the present invention may have an elongated catheter body with a proximal end and a distal end, and at least one spiral centering device attached near the distal end of the catheter. The spiral centering device may have a proximal end and a distal end, and at least one spiral strut extending therebetween. The spiral centering device has a smaller first size for insertion into a lumen, a larger second size for expanding to substantially equal the size of the lumen of the vessel, and a plurality of intermediate sizes in between.

The spiral centering device may be employed in any suitable type of flexible elongated medical device product, including catheters, cannulas, guidewires, and endoscopes. Although the spiral centering catheter may be utilized in conjunction with any suitable type of device, for ease of explanation, the exemplary embodiments described below will refer to a balloon catheter and stent delivery system.

Figure 1:
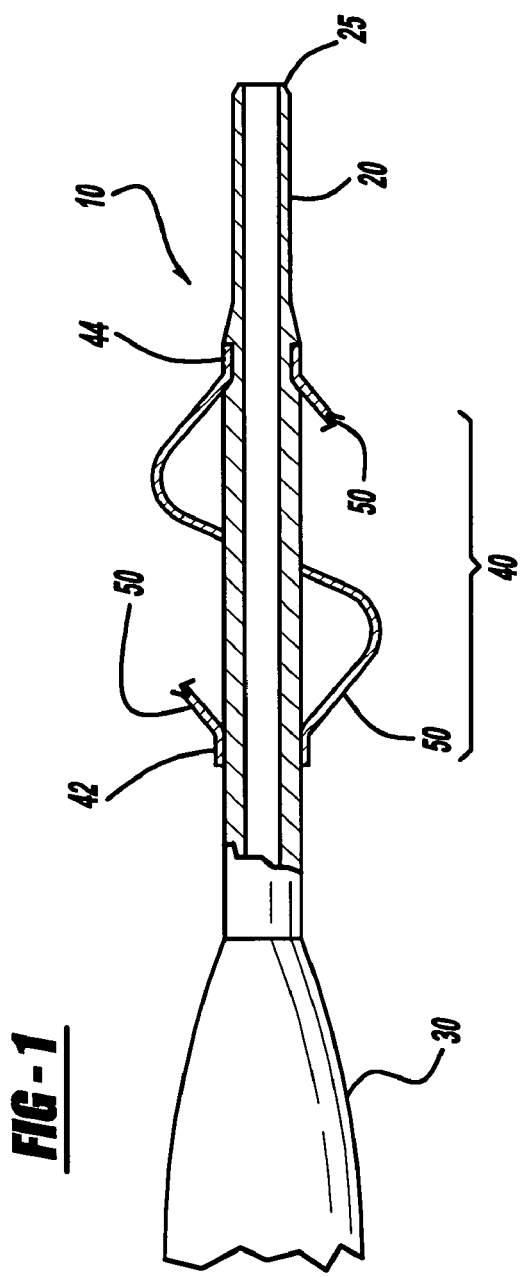
FIG. 1 is a diagrammatic, partial, enlarged, cross-sectional view of an example embodiment of a centering catheter, with a spiral centering device on a balloon catheter.

While the present invention may be realized in a number of exemplary embodiments, for ease of explanation, two exemplary embodiments will be described in detail. Referring to the drawing figures, there is illustrated in FIG. 1 a spiral centering catheter 10. The spiral centering catheter 10 has an inner member 20, which extends longitudinally through the spiral centering catheter 10; a catheter tip 25; at least one spiral centering device 40 attached to the circumference of the inner member 20. An angioplasty balloon 30 may be provided, attached to the inner member 20 proximal to the spiral centering device 40.

Each spiral centering device 40 has a proximal end 42 and a distal end 44 which is affixed to inner member 20, and at least one spiral arm or strut 50 extending therebetween. If more than one strut is provided, the struts 50 may be equally spaced or unequally spaced. Strut 50 may be longitudinal or circumferential, or any number of other suitable configurations. As illustrated in FIG. 1, the spiral centering device 40 has a larger size that substantially equals the size of the lumen, and substantially exceeds the size of the inner member 20. Therefore, the spiral centering device 40 may tend to center the tip 25 of the centering catheter 10 in the lumen during and throughout insertion into the body passage or vessel, until the treatment location is reached.

The spiral centering device 40 may be made from any number of suitable materials including stainless steel or may be made from a superelastic alloy such as Nitinol. The spiral centering device 40 may be coated with any number of suitable materials, which may include a lubricious or biologically compatible or bioactive coating. The spiral centering device 40 may be removably or permanently attached to the inner member 20. The spiral centering catheter may be any suitable configuration catheter, and may have an over-the-wire or rapid exchange configuration.

As illustrated in FIG. 1, the spiral centering catheter may be advanced into the lumen of a body passage or vessel with the centering device 40 tending to expand to make contact with the walls of the lumen. The spiral centering device 40 thus serves to center the distal portion of the catheter 10 and its inner member 20 as it is pushed through the vasculature or other anatomy to the treatment site. The spiral strut(s) 50 are compressible and allow the centering device 40 to vary its diameter as the lumenal diameter varies, while tending to keep the catheter tip 25 of the spiral centering catheter 10 centered in the lumen. This may facilitate the pushability and trackability of the spiral centering catheter 10 as it traverses the vasculature or other anatomy.

Figure 2:
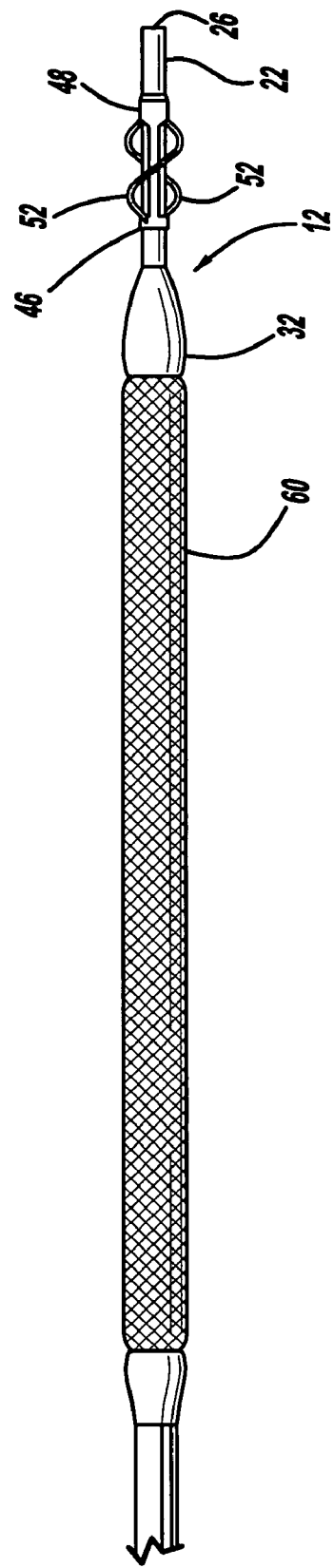
FIG. 2 is a diagrammatic, partial, enlarged, cross-sectional view of an example embodiment of a centering device, with a spiral centering device on a stent delivery system.

FIG. 2 illustrates another example embodiment made in accordance with the present invention. In this example embodiment, a spiral centering catheter 12 is a stent delivery system which has an inner member 22, extending longitudinally through the spiral centering catheter 12; a catheter tip 26; at least one spiral centering device 38 attached to the circumference of the inner member 22; an angioplasty balloon 32 attached to the inner member 22 proximal to the at least one spiral centering device 38; and a stent 60 mounted on the angioplasty balloon 32.

Each spiral centering device 38 has a proximal end 46 and a distal end 48 which is affixed to inner member 22, and at least one strut 52 extending therebetween. If more than one strut is provided, struts 52 may be equally or unequally spaced. Strut 52 may be a longitudinal spiral, or a circumferential spiral, or any number of other suitable configurations. As illustrated in FIG. 2, the spiral centering device 38 has a larger size that substantially equals the size of the lumen, and substantially exceeds the size of the inner member 22. Therefore, the spiral centering device 38 tends to center the catheter tip 26 of the spiral centering catheter 12 in the lumen during and throughout insertion into the vessel, and during stent deployment. Another centering device may also be added to the centering catheter 12 at the proximal end of the stent 60, to further facilitate uniform stent deployment.

The spiral centering device may be made from any number of suitable materials including stainless steel, or may be made from a superelastic alloy such as Nitinol. The resilient outward force of the material may be increased, and/or the size of the centering device may be increased, to enhance the stabilization of the system during stent delivery and deployment.

The centering device may also be coated with any number of suitable materials, and may be coated with a lubricious or biologically compatible or active coating. The spiral centering device may be removably or permanently attached to the inner member. The spiral centering catheter may be any suitable configuration catheter, including an over-the-wire or rapid-exchange catheter. The stent may be a balloon expandable stent, or a self-expanding stent.

As illustrated in FIG. 2, the spiral centering catheter 12 may be a stent delivery system that is advanced into the lumen of a vessel, with the spiral centering device 38 tending to expand to make contact with the walls of the lumen. The spiral centering device 38 thus serves to center the distal end of the catheter 12 and its inner member 22 as it is pushed through the vasculature or other anatomy to the treatment site. The strut 52 is compressible and allows the spiral centering device 38 to vary its size as the lumen size varies, while always tending to keep the catheter tip 26 of the centering catheter 12 centered in the lumen. This may facilitate the pushability and trackability of the centering catheter 12 as it traverses the vasculature or other anatomy. When the treatment site is reached, the spiral centering device 38 may tend to stabilize the stent delivery system in the lumen of the body passage to help uniform stent 60 deployment.

Figure 3:
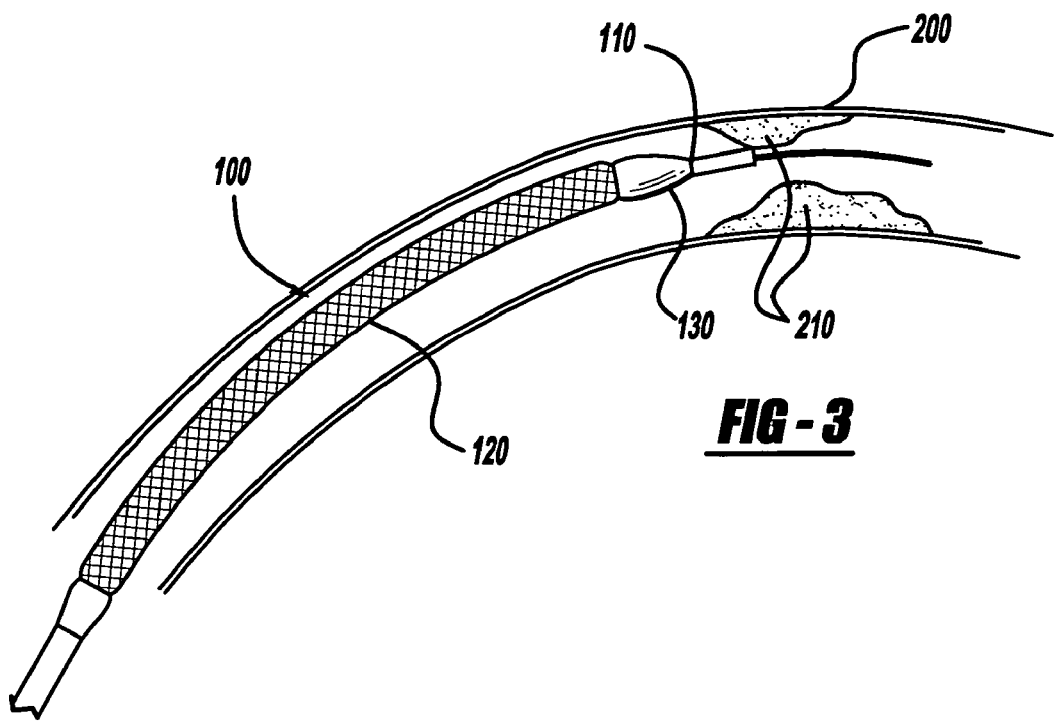
FIG. 3 is a diagrammatic, partial, enlarged, cross-sectional view of a stent delivery system catheter in an irregular and narrowed lumen of a curving vessel.

There is illustrated in FIG. 3 a catheter 100 that does not have a spiral centering device, in an irregular and narrowed lumen of a vessel 200. The lumen may be narrowed by plaques and other deposits 210 on the lumenal surface. The tip 110 of the 100 may therefore become uncentered and may "catch" on the lumenal surface or the lesion 210. Delivery of the catheter 110 to the desired position in the lumen of the vessel may be difficult. In addition, deployment of a stent 120 (shown mounted on a balloon 130) may not be perfectly uniform.

Figure 4:
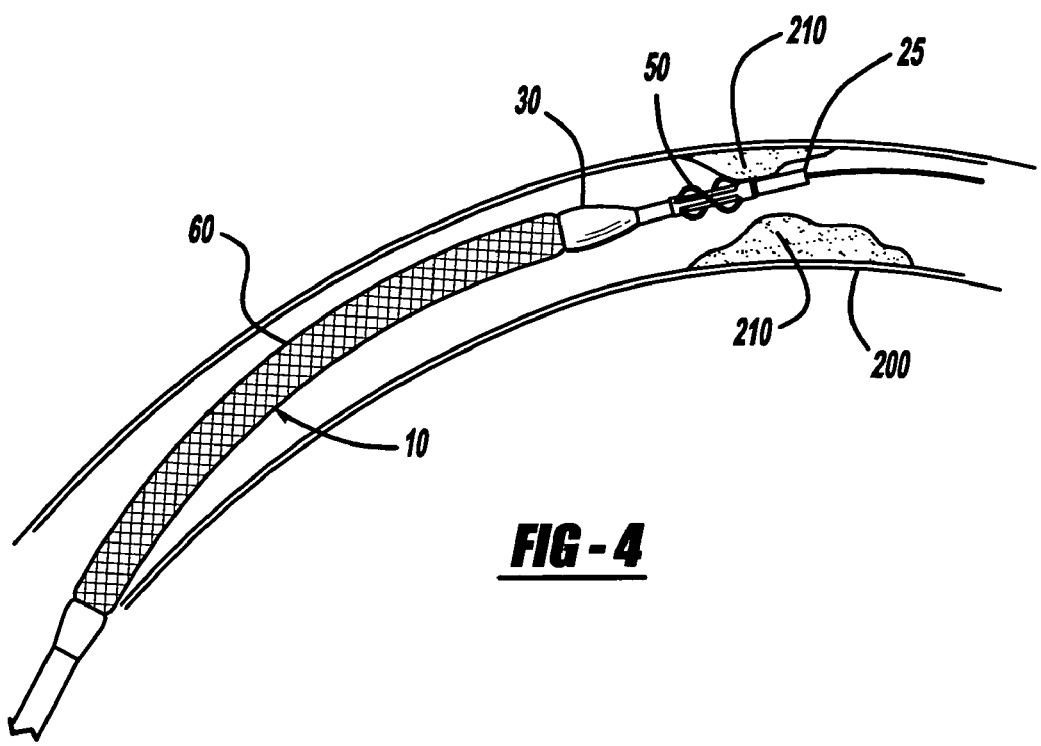
FIG. 4 is a diagrammatic, partial, enlarged, cross-sectional view of an example embodiment of a centering catheter, with a spiral device on a stent delivery system in an irregular and narrowed lumen of a curving vessel.
Figure 5:
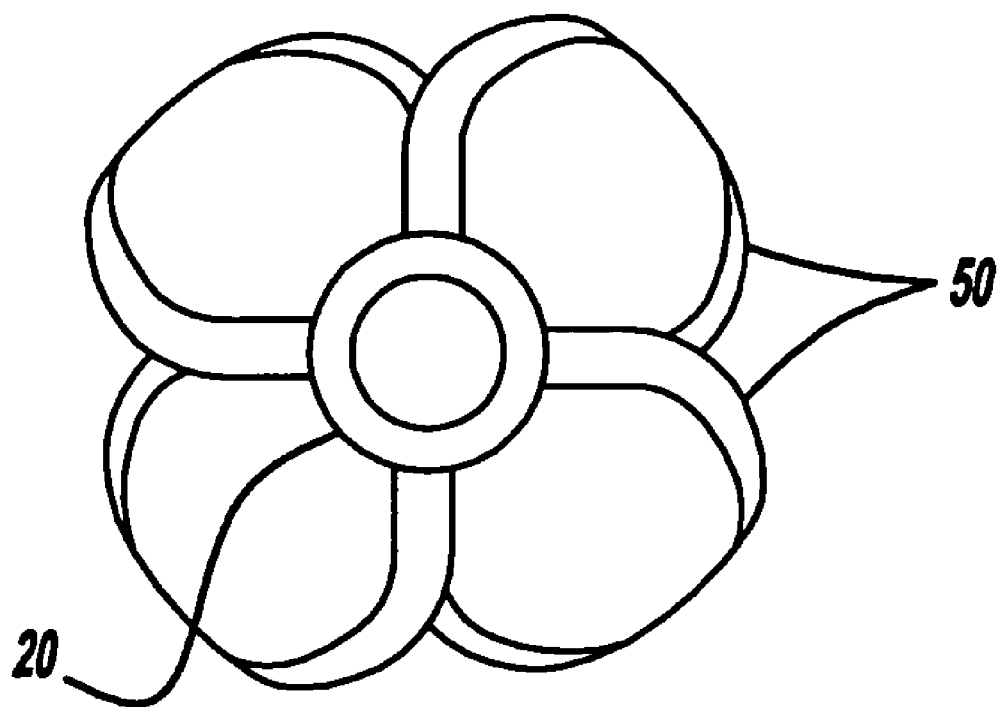
FIG. 5 is an end view of a distal end of a spiral centering catheter.

There is illustrated in FIG. 4 a spiral centering catheter 10 with a centering device 40 on a stent delivery system in an irregular and narrowed lumen of a vessel 200. The lumen may be narrowed by plaques and other deposits 210 on the lumenal surface. Delivery of the spiral centering catheter 10 to the desired position in the lumen of the vessel may be facilitated by the presence of the spiral centering device 40, which tends to center the tip of the catheter 25 in the lumen of the vessel 200. Deployment of a stent 60, shown mounted on a balloon 30, may be facilitated by the presence of at least one spiral centering device 40, which tends to center the catheter 10 within the vessel and facilitate uniform stent deployment.

Although shown and described are what are believed to be the preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cover all modifications that may fall within the scope of the appended claims.

What is claimed is:

1. A catheter for insertion into a lumen to treat a patient, the catheter comprising: an elongated catheter body having a proximal end and a distal end, an outer dimension and an inner dimension; and at least one spiral centering arm attached near the distal end of the catheter, the spiral centering arm having and extending between a proximal end and a distal end, the spiral centering arm having a smaller first size for insertion into a lumen; a larger second size for expanding to substantially equal the size of the lumen, and to center the catheter in the lumen; and a plurality of intermediate sizes there between; the spiral centering arm tending to resiliently expand from a smaller size to a larger size, wherein the centering arm extends in a spiral around a longitudinal axis of the catheter in a spiral pattern between the centering arm proximal and distal ends; the spiral centering arm is made from Nickel-Titanium alloy.

2. The catheter according to claim 1, further comprising at least one additional spiral centering arm.

3. The catheter according to claim 1, wherein the spiral centering arm is permanently or removably attached to the distal end of the catheter.

4. The catheter according to claim 1, wherein the catheter further comprises a balloon.

5. The catheter according to claim 1, wherein the catheter further comprises a stent.

6. The catheter according to claim 5, wherein the stent is a balloon expandable stent.

7. The catheter according to claim 5, wherein the stent is a self-expanding stent.

8. The catheter according to claim 1, wherein the catheter further comprises a guidewire lumen in an over-the-wire configuration.

9. The catheter according to claim 1, wherein the catheter further comprises a guidewire lumen in a rapid exchange configuration.

10. The catheter according to claim 1, wherein the catheter defines multiple lumens.

11. The catheter according to claim 1, wherein the spiral centering arm is coated with a lubricious coating.

12. The catheter according to claim 1, wherein the spiral centering arm is coated with a biologically compatible coating.

13. A method of inserting a catheter into a body lumen, advancing the catheter to a desired treatment site within the body lumen, and delivering a stent, comprising the steps of:

a) inserting a guidewire into a body lumen, the guidewire having a proximal end and a distal end, and advancing the guidewire through the body lumen past a desired treatment site;

b) providing a catheter having a proximal end and a distal end, defining a lumen, an outer dimension and an inner dimension, and having at least one spiral centering arm attached near the distal end of the catheter, the spiral centering arm having and extending between a proximal end and a distal end, the spiral centering arm tending to resiliently expand from a first smaller size to a second larger size substantially equal to the size of the lumen, and tending to thereby center the catheter in the lumen;

c) inserting the proximal end of the guidewire into the distal end of the catheter lumen, and slidably advancing the catheter over the guidewire until the catheter reaches the desired treatment site, with the spiral centering arm making contact with the body lumen, and the spiral centering arm resiliently expanding between the smaller first size and the larger second size as the size of the lumen varies, and the spiral centering arm tending to center the distal end of the catheter in the lumen; and d) deploying the stent in the body lumen, with the spiral centering device tending to center the catheter in the lumen during deployment of the stent.

* * * * *